US012788874B2

(12) United States Patent
Morrison

(10) Patent No.: US 12,788,874 B2
(45) Date of Patent: Nov. 10, 2026

(54) WEARABLE ARTICLE TO HOLD A VENTRICULAR ASSIST DEVICE CONTROLLER

(71) Applicant: Chris Morrison, New Bedford, MA (US)

(72) Inventor: Wayne Morrison, New Bedford, MA (US)

( * ) Notice: Subject to any disclaimer, the term of this patent is extended or adjusted under 35 U.S.C. 154(b) by 120 days.

(21) Appl. No.: 17/683,278

(22) Filed: Feb. 28, 2022

(65) Prior Publication Data

US 2022/0273865 A1 Sep. 1, 2022

Related U.S. Application Data

(60) Provisional application No. 63/154,064, filed on Feb. 26, 2021.

(51) Int. Cl.

| | |
|---|---|
| ***A61M 5/14*** | (2006.01) |
| ***A41D 13/00*** | (2006.01) |
| ***A41D 27/20*** | (2006.01) |
| ***A61M 5/142*** | (2006.01) |

(52) U.S. Cl.

CPC ..... *A61M 5/14244* (2013.01); *A41D 13/0012* (2013.01); *A41D 27/20* (2013.01)

(58) Field of Classification Search

CPC ........ A61M 5/14244; A61M 2209/088; A41D 13/1245; A41D 13/1281; A41D 13/0012; A41D 27/205; A41D 27/201; A45F 5/022; A45F 2003/144; A45F 2200/05; A45F 5/00; A45F 5/021; A45F 3/04; Y10S 224/93

See application file for complete search history.

(56) References Cited

U.S. PATENT DOCUMENTS

| | | | | |
|---|---|---|---|---|
| 4,502,155 | A * | 3/1985 | Itoi | A45F 4/12 2/94 |
| 6,105,171 | A * | 8/2000 | Niedermeyer | A41D 13/129 2/114 |
| 6,131,199 | A * | 10/2000 | Bugel | A41D 13/0012 2/102 |
| 7,000,255 | B1 * | 2/2006 | Baacke | A41D 13/0012 2/94 |
| 10,264,831 | B1 * | 4/2019 | Hemker | A61F 5/03 |
| 2010/0072241 | A1 * | 3/2010 | Brown | A45F 3/08 224/660 |
| 2011/0000944 | A1 * | 1/2011 | Hood | A41D 27/20 2/102 |
| 2012/0150085 | A1 * | 6/2012 | Kayser | A61F 5/026 602/19 |
| 2013/0047312 | A1 * | 2/2013 | Wilson | A41D 13/0012 2/69 |
| 2021/0401094 | A1 * | 12/2021 | Clemens | A41D 13/1245 |

* cited by examiner

*Primary Examiner* — Adam J Waggenspack

(74) *Attorney, Agent, or Firm* — Ballard Spahr LLP

(57) ABSTRACT

The present disclosure is directed to a wearable article for holding a medical device, such as a ventricular assist device, and methods of using and making the same. The wearable article comprises a rear pocket that is upside-down and can further be padded. Other padded pockets can also be provided.

16 Claims, 3 Drawing Sheets

WEARABLE ARTICLE TO HOLD A VENTRICULAR ASSIST DEVICE CONTROLLER

FIELD OF INVENTION

The present disclosure is directed to a wearable article for holding a medical device, such as a ventricular assist device, and methods of using and making the same.

BACKGROUND

A ventricular assist device (VAD)—also known as a mechanical circulatory support device—is an implantable mechanical pump that helps pump blood from the lower chambers of your heart (the ventricles) to the rest of the recipient's body. A VAD is used in patients who have weakened hearts or heart failure. Although a VAD can be placed in the left, right or both ventricles of your heart, it is most frequently used in the left ventricle. When placed in the left ventricle it is called a left ventricular assist device (LVAD).

A VAD consists of a pump, tubes that connect the pump to the heart, a control module (i.e., controller), and a power source. A thin cable connects the pump with the controller. This cable, also called a lead or driveline, comes out of your belly through a small cut in your skin called an exit site. The recipient carries the control module, a battery, and a back-up battery on their body.

Vests, shirts, and harnesses with pockets have been designed to carry the control module and batteries. However, a need exists to make these more discreet, user friendly, and/or comfortable.

SUMMARY OF THE INVENTION

The present disclosure is directed to a wearable article that has an interior-facing rear pocket for receiving a ventricular assist device (VAD) controller that is located in the upper back area between the shoulder blades and methods of making and using the same. The pocket can be upside-down and/or padded for comfort.

One aspect of the present disclosure is a wearable article for at least partially covering a trunk of a wearer comprising one or two front panels of fabric configured to be located on the front of the wearer during use; a rear panel of fabric configured to be located on the back of the wearer during use; the one or two front panels affixed to the rear panel to define two arm openings and at least partially define a neck opening; a rear pocket formed from a rear pocket panel affixed to the interior face of the rear panel, the opening of the pocket sized to receive a VAD controller; at least one rear strap coupled to the rear panel and configured to prevent the VAD controller when in the pocket from falling out of the pocket. In some embodiments, the rear pocket panel is affixed to the rear panel so that the opening of the rear pocket is at the bottom. In other words, the pocket can be upside down. In the same or different embodiments, the rear pocket panel can also be padded for the wearers comfort.

Another aspect of the present disclosure includes methods of using the wearable article. The user of the article can place the VAD controller or one or more of the batteries in the rear pocket. Two or more pockets may be located nearer the waistline, and the VAD controller or one or more of the batteries can also be placed in the two or more pockets at the waistline. The article can be worn underneath another article of clothing or can be the outermost article of clothing. No wires, controllers, or batteries are exposed or visible to others when properly used.

Yet a third aspect of the present disclosure making the wearable article. In some embodiments, the wearable article can be made by knitting, sewing, and/or laser cutting.

DRAWINGS

The accompanying drawings, which are incorporated in and constitute a part of this specification, illustrate embodiments of the invention and together with the description, serve to explain the principles of the invention.

DETAILED DESCRIPTION

Figure 1:
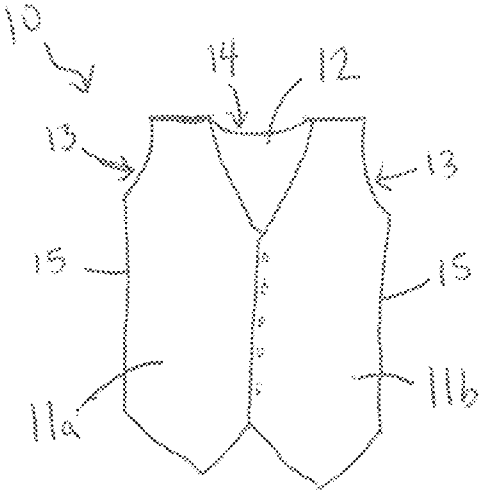
FIG. 1 illustrates the front view of an embodiment of a wearable article.

FIGS. 1, 2, 3A, 3B, 4A, and 4B illustrate various aspects of an embodiment of a wearable article 10 in accordance with the present disclosure. The wearable article depicted is a vest. FIG. 1 illustrates a front view of the wearable article 10. A wearable article 10 can partially, predominantly (more than 50% coverage), or completely cover the trunk of the wearer.

Shown in FIG. 1 is the front view of the wearable article 10. In the embodiment shown, a front panel 11 is shown and is configured to be located on the front trunk portion of the wearer during use. A single or multiple panels of fabric or a single panel of fabric can be used to form a the front panel 11. In the embodiment shown, a first and second panel of fabric 11*a* and 11*b* form the front panel 11. In other embodiments (not shown), a knit shirt may only require a single front panel. Front panel 11 be configured to partially, predominantly (more than 50% coverage), or completely cover the front surface of the trunk of the wearer.

Figure 2:
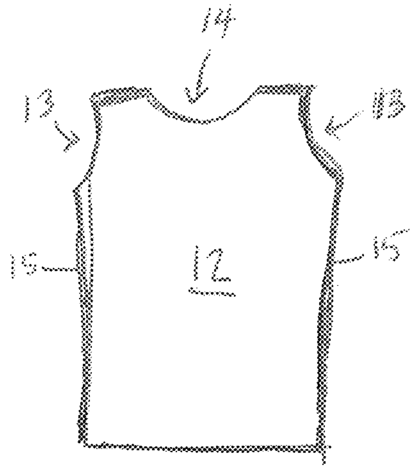
FIG. 2 illustrates the rear view of an embodiment of the wearable article of FIG. 1.

Shown in FIG. 2 is a rear view of the wearable article 10. In the embodiment shown, a rear panel 12 is configured to be located on the back of the wearer during use. A single or multiple panels of fabric can be used to form a rear panel 12. Rear panel 12 can be configured to partially, predominantly (i.e., more than 50% coverage), or completely cover the rear surface of the trunk of the wearer.

The front panel 11 is affixed to the rear panel 12 to define two arm openings 13 and at least partially define a neck opening 14. The embodiment shown in the FIGS. 1 and 2 comprises front panels 11*a* and 11*b* and rear panel 12 configured to be a vest when attached on the sides 15 and the shoulder 16 except at the arm openings 13 and neck opening 14.

Figure 3A:
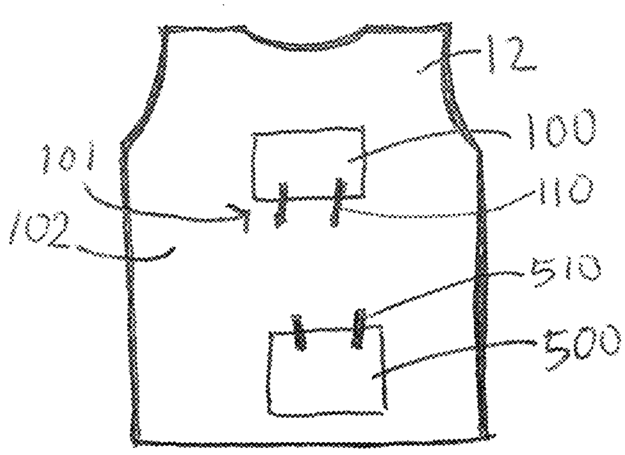
FIG. 3A illustrates the interior face of the rear panel of the embodiment of the wearable article of FIG. 1.
Figure 3B:
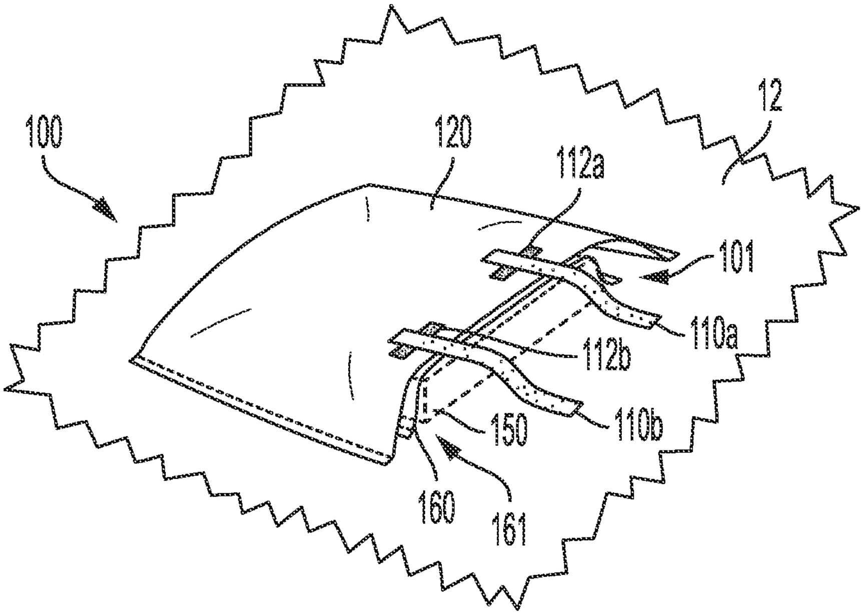
FIG. 3B illustrates a close-up view of the rear pocket on the rear panel shown in FIG. 3A.

Configured to hold an object, such as a VAD controller, a rear pocket 100 is formed from a rear pocket panel 120 affixed to the interior face of the rear panel 12. An embodiment of a rear panel 12 with a rear pocket 100 is shown in FIG. 3A and a close up view of the rear pocket 100 is shown in FIG. 3B. The pocket 100 is located on the rear panel 12 such that when the article 10 is worn, the rear pocket 100 is located in the middle of the back and on the upper half of the trunk of the wearer. In some embodiments, the rear pocket 100 is located between the shoulder blades. In FIG. 3B, an object 150 is shown located within the rear pocket 100.

The rear pocket 100 can be right side up or upside down. The embodiment shown in FIG. 3A illustrates the rear pocket 100 that is upside down. In other words, the rear pocket 100 has an opening 101 at the bottom of the rear pocket panel 120. In some embodiments, as shown in FIG. 3B, the rear pocket 100 is configured to hold a VAD controller 150, and as such, the opening 101 of the pocket 100 is sized to receive a VAD controller. To ensure that the VAD controller remains securely in an upside down pocket, a fastener 110 configured for supporting the VAD controller to prevent it from falling out of the pocket 100 can be provided. For example, a hook and loop tape (Velcro®) can be affixed to the rear pocket panel 120 adjacent the opening 101 and the corresponding pieces can placed on the interior face of the rear panel 12. In embodiments, the fastener can comprise one or more rear straps, such as rear straps 110*a* and 100*b*, coupled to the rear panel 12 and the rear pocket panel 120, which are releasable to at least one of the rear panel 12 and the rear pocket panel 120 and configured to prevent an object 150, such as a VAD controller, when in the pocket from falling out of the pocket. The rear straps 110*a*, 110*b* can be releasable by way of a hook and loop tape 112*a*, 112*b* or a snap button (not shown), for example.

In some embodiments, the rear pocket panel 120 is padded to provide cushioning between the wearer and the object 150 in the pocket, such as the VAD controller. Such padding can be sufficiently thick to provide for comfort to the wearer, particularly when the wearer rests his/her back up against a chair or wall, for example. The padded rear pocket panel is sized and positioned relative to the VAD controller securement member to provide cushioning over all edges of the VAD controller during use.

For embodiments with the a padded rear pocket 100, for example, the article 10 can further comprise an object securement member 160 (such as a VAD securement member) located within the rear pocket 100 and configured to limit left to right movement of an object, such as a VAD controller 150, within the rear pocket during use. For example, as shown in FIG. 3B, the object securement member 160 is an inner rear pocket formed from a panel of fabric affixed to the interior face of the rear panel 12 or to a face of the rear pocket panel 120 facing the interior face of the rear panel 12 so that the inner rear pocket has an opening at the bottom of the inner rear pocket panel. The opening 161 is smaller than the rear pocket 100 opening 101 yet the opening 161 of the inner rear pocket is also sized to receive the VAD controller 150. In other words, the padded rear pocket panel 100 is wider as measured from the left side to the right side than the inner rear pocket. In embodiments with a rear pocket 100 and an inner rear pocket, the releasable fastener can be coupled to either one of the rear pocket 100 or the inner rear pocket in order to support the object 150.

Additional pockets with fasteners may also be provided in other locations on the wearable article. The pocket can be interior or exterior facing and in any orientation and the opening of the pockets may be in any side or orientation such at an angle, sideways, right side up or upside down. For example, the wearable article can also comprise a second rear pocket 500 that is the same as rear pocket 100 except positioned on the lower half of the wearer's trunk such as adjacent the sacrum area. This pocket 500 can be right side up or upside down. In the embodiment shown, the pocket is right side up. The second rear pocket can be formed from a second rear pocket panel affixed to the interior face of the rear panel to form a pocket. The second rear pocket 500 can have an opening of the pocket at the top of the second rear pocket panel. The pocket can be sized to receive the object 150 so it can be the same size as the rear pocket 100 or the inner rear pocket, for example. The second rear pocket panel can also padded to provide cushioning between the wearer and the object held therein, such as a VAD controller 150. One or more fasteners 510 such as fastener 110 described above can be configured to prevent the object within from escaping the pocket can be included. The fastener 510 can be coupled to at least one of the rear panel 12 and the second rear pocket 500 and releasable coupled to one or the other.

And like rear pocket 100 if padded, the article 10 can further comprise a second object securement member that is the same as the securement member 160 except that it is located within the second rear pocket 500 and is right side up. As such, the second object securement member can be a second inner pocket formed from rear pocket panel affixed to the interior face of the rear panel or to a face of the second rear pocket panel facing the interior face of the rear panel so that the second inner rear pocket has an opening at the top of the inner pocket panel. Also, the opening of the second inner rear pocket can be sized to receive an object, such as a VAD controller 150 but is narrower as measured from the left side to the right side than the outer rear pocket 500.

Figure 4A:
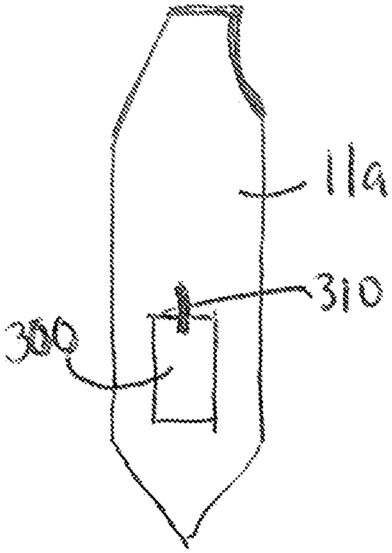
FIGS. 4A and 4B illustrate an interior face of two front panels of the embodiment of the wearable article in FIG. 1.
Figure 4B:
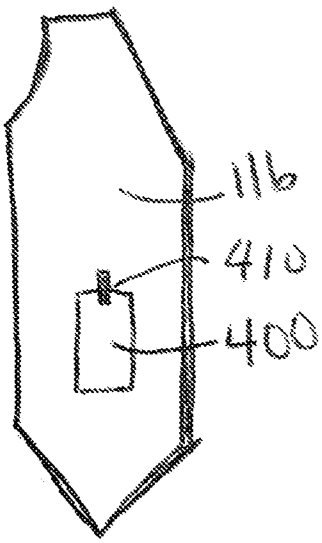

One or more pockets can also be located on one or both of the front panels 11*a*, 11*b*. As shown in FIGS. 4A and 4B, the front pockets 300, 400 can be like that of the other pockets but may not be padded as a padded pocket is not as useful on the front panel. The front pockets 300 or 400 can be sized to hold an object such as a VAD controller or a VAD battery. The front pockets 300 or 400 can be a breast pocket or located on the lower half of the trunk. A fastener 310, 410 as described above can also be included to keep an object held within the front pocket 300 or 400 secure.

Figure 5:
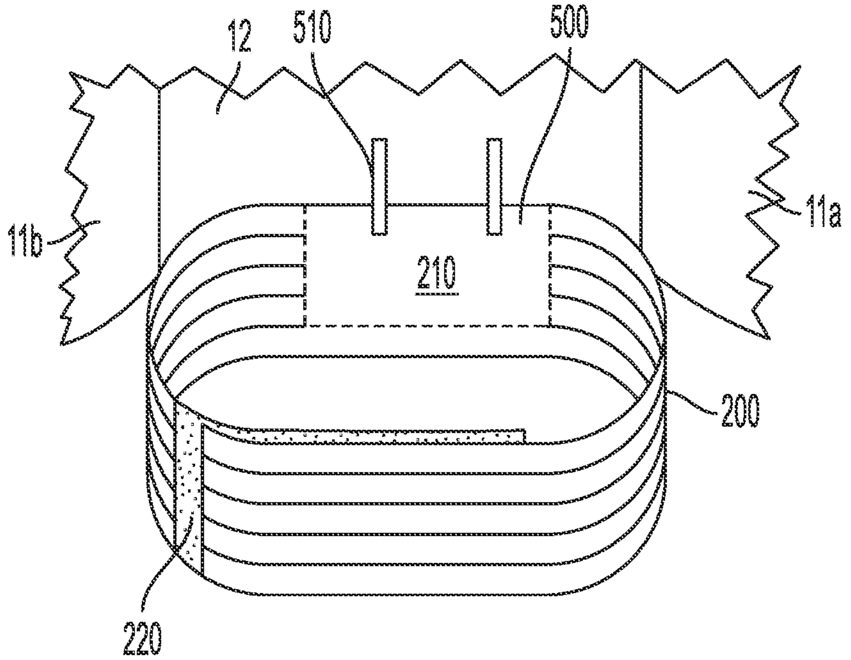
FIG. 5 illustrates a support belt of a second embodiment of a wearable article similar to that of FIG. 1 but with the addition of a support belt.

In some embodiments, as shown in FIG. 5, the wearable article is like that of FIG. 1 but can further comprise a lumbar support belt/brace 200 to distribute the load of the wearable article and object(s) carried in the pockets therein about the hips and take some load off of the shoulders. The lumbar support belt 200 can be affixed to the rear panel 12 below the rear pocket 100. The lumber support belt/brace 200 can comprise a wide elastic band that wraps around the lower back and can comprise one or more fasteners 220, such as a hook and loop fastener, to firmly wrap and secure the band/brace around the lower back.

In some embodiments, a portion of the support belt 200 serves as the second rear pocket panel 210. In other words, the support belt 200 is secured to the rear panel forming a U-shaped seam such that the support belt 200 together with the rear panel 12 form a pocket wherein an object, such as a VAD controller can be held.

The rear pocket 100 of the above described device is useful when oriented upside down because the VAD controller wires that connect to the VAD extend downward and can easily extend underneath the wear's arm to connect to the chest. The position at the upper center of the back also allows the VAD controller to be worn without other's being aware of the VAD controller's presence and with less obstruction to the wearer. In addition, if a user wanted to move the VAD controller, the user could reach back, release the fastener, and easily place it in another pocket without having to remove the article 10 or disconnect any wires.

A method using the wearable article can comprise placing a VAD controller in rear pocket 100 of a wearable article as described above. The wires of the VAD controller extending from the opening of the rear pocket 100. The method can further comprise extending the wire(s) from the VAD controller, underneath an arm, and to the VAD connector that is located on the wearer's chest and connecting the VAD wire thereto. The method can further comprise removing the VAD controller 150 from rear pocket 100 and placing it in the second rear pocket 500 or a front pocket 300 or 400 while wearing the wearable article 10.

A method of making the wearable article described above can comprise attaching a rear pocket panel to an interior face of the rear panel of a wearable article at a location that would be at least partially between the shoulder blades when worn by the user. The rear pocket being like that described above and shown in FIGS. 3A and 3B. A method can also comprise attaching a support belt to the wearable article and forming a second rear pocket between the support belt and the rear panel. The attachment points of the support belt to the rear panel can be the seams of the pocket.

Although the present wearable article and methods of using the same has been described with reference to specific details of certain embodiments thereof, it is not intended that such details should be regarded as limitations upon the scope of the invention except as and to the extent that they are included in the accompanying claims.

I claim:

1. A wearable article for at least partially covering a trunk of a wearer comprising one or two front panels of fabric configured to be located on the front of the wearer during use;

a rear panel of fabric configured to be located on the back of the wearer during use;

the one or two front panels affixed to the rear panel to define two arm openings and at least partially define a neck opening;

a rear pocket formed from a rear pocket panel affixed to the interior face of the rear panel so that the rear pocket has an opening at the bottom of the pocket panel, the opening of the pocket sized to receive a ventricular assist device (VAD) controller;

an inner rear pocket formed from a panel of fabric affixed to the interior face of the rear panel or to a face of the rear pocket panel facing the interior face of the rear panel so that the inner rear pocket has an opening at the bottom of the inner rear pocket panel, the opening of the inner rear pocket is sized to receive the VAD controller, wherein the opening of the rear pocket panel is wider as measured from the left side to the right side than the opening of the inner rear pocket; and at least one rear pocket fastener coupled to the rear panel or the inner rear pocket panel and configured to prevent the VAD controller when in the pocket from falling out of the pocket, wherein the rear pocket panel is padded to provide cushioning between the wearer and the VAD controller over all edges of the VAD controller during use;

wherein the rear pocket panel consists of one or two layers of fabric panels and a padded layer configured to provide cushioning between the wearer and the VAD controller over all edges of the VAD controller during use; and wherein the inner rear pocket is configured to limit left to right movement of the VAD controller within the rear pocket during use.

2. The article of claim 1, wherein the at least one rear pocket fastener is releasably coupled to at least one of the rear panel and the rear pocket.

3. The article of claim 1, wherein the real pocket panel is positioned on the rear panel such that the rear pocket panel is located on the upper half of the trunk of the wearer during use.

4. The article of claim 3, comprising a second rear pocket formed from a second rear pocket panel affixed to the interior face of the rear panel to form a pocket that has an opening of the pocket at the top of the second rear pocket panel, the pocket sized to receive a VAD controller, wherein the second rear pocket panel is positioned on the lower half of the wearer's trunk.

5. The article of claim 4, wherein the second rear pocket panel is padded to provide cushioning between the wearer and the VAD controller.

6. The article of claim 5, further comprising a second VAD controller securement member located within the second rear pocket and configured to limit left to right movement of the VAD controller within the second rear pocket during use.

7. The article of claim 6, wherein the second VAD controller securement member is a second inner pocket formed from rear pocket panel affixed to the interior face of the rear panel or to a face of the second rear pocket panel facing the interior face of the rear panel so that the second inner rear pocket has an opening at the top of the inner pocket panel, the opening of the second inner rear pocket is sized to receive the VAD controller, wherein the second padded rear pocket panel is wider as measured from the left side to the right side than the inner rear pocket.

8. The article of claim 7, wherein the second padded rear pocket panel is sized and positioned relative to the second VAD controller securement member to provide cushioning over all edges of the VAD controller during use.

9. The article of claim 6, wherein the at least one pocket fastener is releasably coupled to at least one of the rear panel and the second rear pocket.

10. The article of claim 1, wherein the one or two front panels are coupled to one or more front pocket panels to form a pocket sized to receive one battery for the VAD controller.

11. The article of claim 1, wherein the one or two front panels is two front panels and wherein each of the two front panels are coupled to a front pocket panel to form a pocket sized to receive one battery for the VAD controller.

12. The article of claim 10, comprising at least one front pocket fastener per front pocket panel coupled to the front panel and one of the front pocket panels, wherein the at least one front pocket fastener is releasably coupled to at least one of the front panel and the front pocket panel.

13. The article of claim 1, further comprising a lumbar support belt affixed to the rear panel below the rear pocket panel.

14. The article of claim 13, wherein portion of the support belt coupled to the rear panel to form a second rear pocket panel.

15. The article of claim 13, wherein the article is a vest.

16. A method using the wearable article of claim 1, comprising placing the wearable article on a user and connecting a VAD connector to the VAD controller; placing the VAD controller in the rear pocket.

* * * * *